(12) United States Patent
Shafir

(10) Patent No.: US 6,371,930 B1
(45) Date of Patent: Apr. 16, 2002

(54) METHOD AND APPARATUS FOR MAPPING CONTOURED SURFACES PARTICULARLY USEFUL IN PREPARING ARTIFICIAL DENTAL CROWNS

(75) Inventor: Roni Shafir, Tel Aviv (IL)

(73) Assignee: Shafir Production Systems Ltd., Kfar Saba (IR)

( * ) Notice: Subject to any disclaimer, the term of this patent is extended or adjusted under 35 U.S.C. 154(b) by 0 days.

(21) Appl. No.: 09/691,888

(22) Filed: Oct. 20, 2000

(51) Int. Cl.[7] ................................................. A61B 5/00
(52) U.S. Cl. ..................................... 600/590; 433/202.1
(58) Field of Search ................................. 600/587, 590; 433/202.1, 214, 229

(56) References Cited

U.S. PATENT DOCUMENTS 4,997,369 A * 3/1991 Shafir ........................... 433/72
5,440,393 A * 8/1995 Wenz ........................... 600/590
5,861,955 A * 1/1999 Gordon ........................ 356/360
5,957,868 A * 9/1999 Case et al. ................... 600/590
6,268,923 B1 * 7/2001 Michniewicz et al. ...... 356/512

* cited by examiner

Primary Examiner—Max Hindenburg

(57) ABSTRACT

A method and apparatus for measuring a contoured surface, particularly the outer surface of a tooth to receive an artificial crown, by means of a probe having at least one light source, preferably three light sources at different known locations with respect to the probe contact surface; and a light sensor device at a known location with respect to the contoured surface to be mapped. The probe is moved over the contoured surface through a plurality of positions, with the probe contact surface in contact with the contoured surface at each of the positions; and the location in space of each of the light sources is measured at each of these positions. The measured locations of the light sources are used for computing the location of the probe contact surface with respect to the known location of the light sensor device.

23 Claims, 7 Drawing Sheets

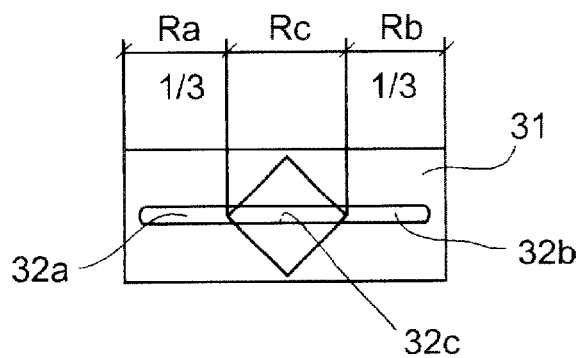
Fig. 5a
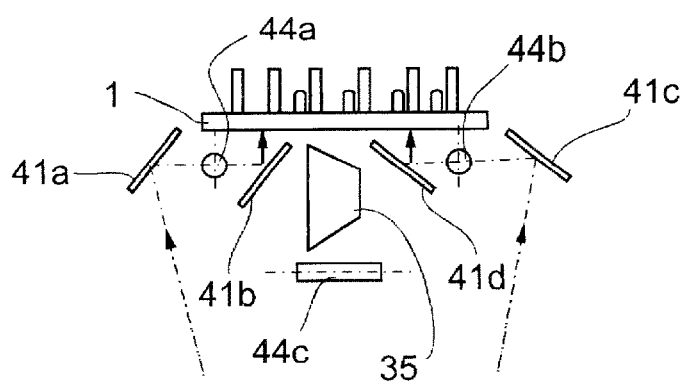
Fig. 5b
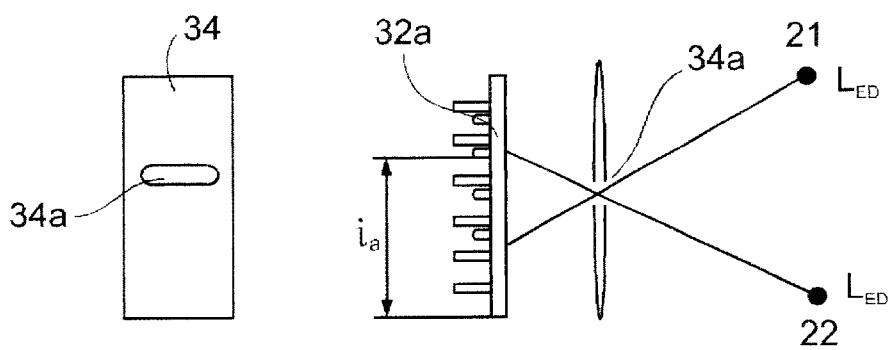
Fig. 6a
Fig. 6b
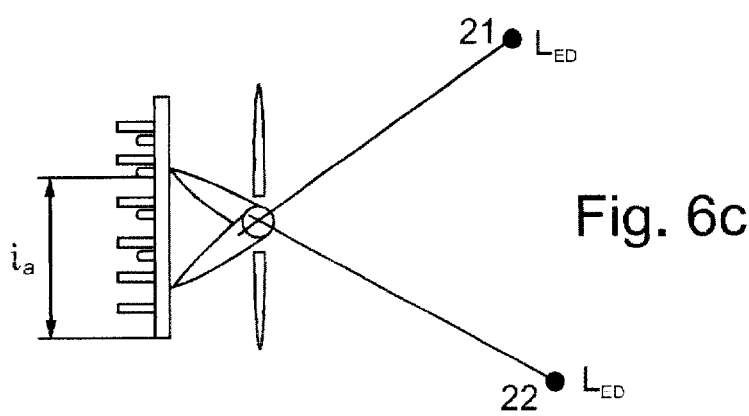
Fig. 6c

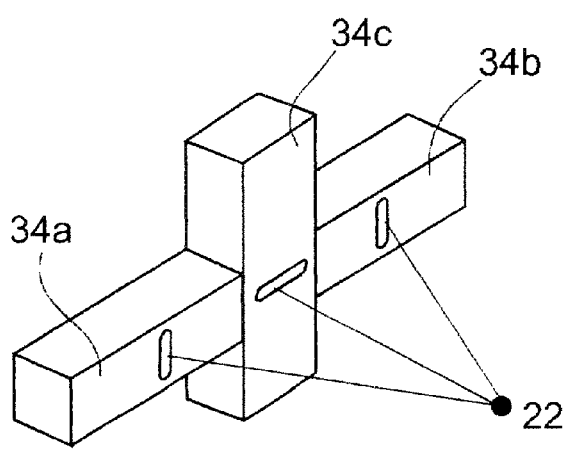 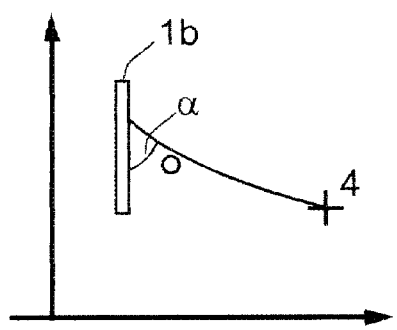
Fig. 11a  Fig. 11b
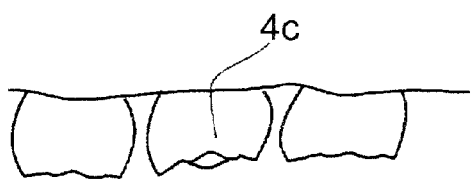
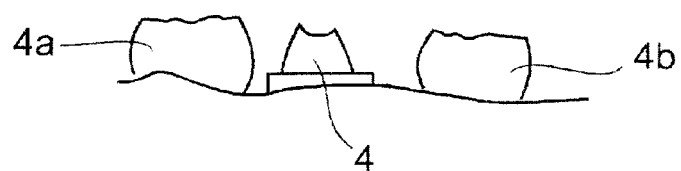
Fig. 12

METHOD AND APPARATUS FOR MAPPING CONTOURED SURFACES PARTICULARLY USEFUL IN PREPARING ARTIFICIAL DENTAL CROWNS

FIELD AND BACKGROUND OF THE INVENTION

The present invention relates to a method and apparatus for mapping contoured surfaces. The invention is particularly useful in dental applications, e.g., for preparing artificial dental crowns, and is therefore described below with respect to such an application.

The preparation of an artificial dental crown has historically been a long and expensive process, involving firstly the preparation of a mold, and then the preparation of a crown from the mold. U.S. Pat. No. 4,997,369, in which the inventor of the present application is a joint-inventor, discloses a method and apparatus for producing an artificial dental crown by using a probe which is mounted in the mouth of the patient to receive the crown. The displacements of the probe are measured as the probe is moved along the surfaces of the teeth required to be mapped for preparing the tooth crown. In such a method, however, mounting the movable probe in the mouth of the patient is inconvenient and uncomfortable to the patient. Moreover, mapping teeth surfaces (or other surfaces) by measuring the movements (as distinguished from positions) of the probe produces errors which are cumulative.

BRIEF SUMMARY OF THE PRESENT INVENTION

An object of the present invention is to provide a method and apparatus for mapping contoured surfaces having advantages in one or both of the above respects and which thereby makes the method and apparatus particularly useful in dental applications.

According to one aspect of the present invention, there is provided a method of mapping a contoured surface, comprising: providing a probe for contacting the contoured surface with at least one light source at a known location with respect to the probe contact surface; providing a light sensor device at a known location with respect to the contoured surface to be mapped; moving the probe over the contoured surface through a plurality of positions with the probe contact surface in contact with the contoured surface at each of the positions; measuring the location in space of each light source at each of the positions; and computing, from the measured location of the light source at each of the positions, the location of the probe contact surface with respect to the known location of the light sensor device.

According to further features in the preferred embodiment described below, the probe is provided with at least three light sources at different known locations with respect to the probe contact surface. Also, the light sensor device includes first, second and third linear arrays of light sensor elements extending along a first axis; and a screen having first, second and third slits. The first and second slits are aligned with the first and second linear arrays of light sensor elements, respectively, but extend along a second axis; and the third slit is aligned with the third linear array of light sensor elements and extends along the first axis. An optical device is provided between the third linear array of light sensor elements and the third slit for diverting the light received from the light sources in the third axis to the first axis.

According to another aspect of the present invention, there is provided apparatus for mapping a contoured surface, comprising: a probe movable to a plurality of positions over and in contact with the contoured surface to be mapped; at least one light source, and preferably three light sources, carried by the probe at different known locations thereof with respect to the contact surface of the probe; a light sensor device mountable at a predetermined location with respect to the contoured surface to be mapped; and a computer controlled by the light sensor device for measuring the locations in space of each of the light sources at each of the plurality of positions, and for computing from the measurements the location of the probe contact surface at each of the positions.

According to further features in the described preferred embodiment, the probe includes a contact detector for detecting the contact of the probe contact surface with the contoured surface to be mapped, and for enabling the computer to measure the locations of the light sources only when the contact detector detects contact of the probe contact surface with the contoured surface.

As will be described more particularly below, although the light sensor device is mounted at a known location with respect to the contoured surface to be mapped, the movable probe is not so mounted, but rather is freely movable over the contoured surface to be mapped. Such an arrangement is particularly useful in dental applications for preparing artificial dental crowns, since an arrangement having an unmounted, freely movable probe is more comfortable to the patient to receive the artificial crown, and is more convenient to the dentist or dental technician for mapping the teeth surfaces to produce the artificial crown. Moreover, such a method and apparatus are inherently capable of higher accuracy since this technique does not produce measurements of the movements of the probe (which measurements would involve cumulative errors), but rather produces direct measurements of the location of the contact surface of the probe at each of the map points, and thereby avoids the cumulation of errors.

Further features and advantages of the invention will be apparent from the description below.

BRIEF DESCRIPTION OF THE DRAWINGS

The invention is herein described, by way of example only, with reference to the accompanying drawings, wherein:

FIG. 5a is a front view, and FIG. 5b is a side view, illustrating the cooperation of the light sensor assembly of FIG. 4a with the optical prism included in the light sensor unit of FIG. 3b;

FIGS. 6a and 6b are side and front views, respectively, which diagrammatically illustrate the cooperation of the light screen with the light sensor assembly in the light sensor unit of FIGS. 3a or FIG. 3b; and FIG. 6c is a side view of an alternative assembly of the light sensor unit of FIG. 3b;

FIGS. 7b and 8b are corresponding geometrical diagrams, helpful in explaining the manner in which the light sensor unit is used for determining the location, in two axes, of each of the light sources at each of the sampled positions of the probe contact surface;

FIG. 11a is an optical diagram, and FIG. 11b is a corresponding geometrical diagram, illustrating the manner in which the screen within the light sensor unit of FIG. 3 is used for determining the location in space of each of the light sources at each of the sample positions of the probe; and FIGS. 12, 13 and 14 are diagrams illustrating the manner in which the described apparatus is used for mapping the outer surfaces of teeth in order to prepare an artificial dental crown.

DESCRIPTION OF A PREFERRED EMBODIMENT

Figure 1:
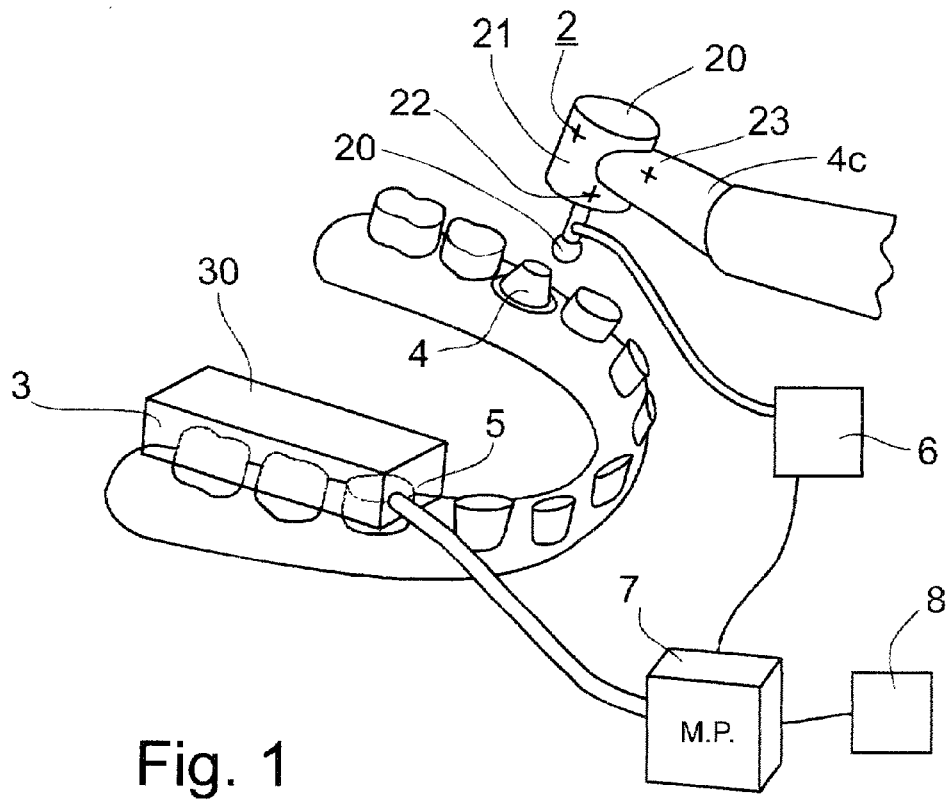
FIG. 1 diagrammatically illustrates one form of apparatus constructed in accordance with the present invention.

The apparatus illustrated in FIG. 1 is intended for directly mapping the outer contoured surface of teeth in a patient's mouth for use in preparing an artificial dental crown or bridge. The illustrated apparatus includes two units: a probe unit, generally designated 2, which is gripped by the dentist or dental technician and freely moved while in direct contact with the tooth (e.g., a ground tooth stub, or implanted post) to receive a crown; and a light sensor unit, generally designated 3, which is mounted on the patient's teeth spaced from the tooth to receive the crown so as to be at a known location with respect to the latter tooth. In FIG. 1, the tooth to receive the crown is indicated at 4, and the remaining teeth including those receiving the light sensor unit 3, are indicated at 5.

FIG. 1 further illustrates a contact detector 6 which detects the contact of the probe 2 with the tooth 4 being mapped. FIG. 1 further illustrates a computer 7, such as a microprocessor, which computes the location in space of the probe contact surface at each of a plurality of positions of that surface to thereby map the outer surface tooth 4 to receive the crown as well as the surfaces of other teeth 5 necessary for the preparation of the crown, as will be described below.

Figure 2:
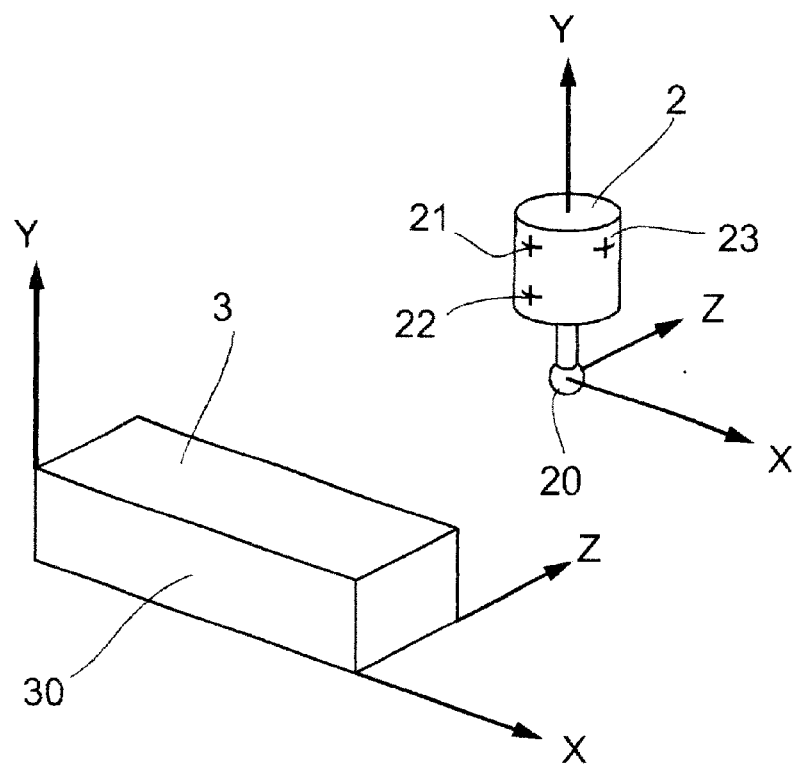
FIG. 2 diagrammatically illustrates the probe unit and light sensor unit in the apparatus of FIG. 1.

As further shown in FIG. 1, and also in FIG. 2, the probe unit 2 includes a tip 20 defining a contact surface which is brought into contact with the outer surface of each tooth being mapped, and three light sources 21, 22, 23, at different known locations with respect to the contact surface 20. As will be described more particularly below, as the probe contact surface 20 is moved over the surface of the tooth being mapped, the light sensor unit 3 measures the location in space of each of the light sources 21–23 at each sampled position. Since the location of each light source is known with respect to the probe contact surface 20, such measured locations of the light sources may be used for determining the location of the probe contact surface 20 with respect to the light sensor device 3 at each sampled position of the probe. The locations of the probe contact surfaces define the contour of the surfaces being mapped and are outputted by the computer 7 as shown at 8 in FIG. 1.

Figure 3A:
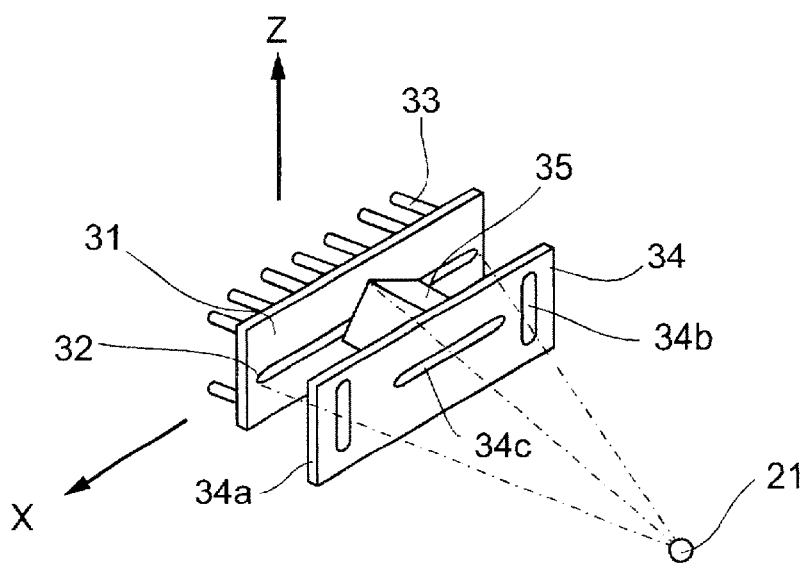
FIGS. 3a and 3b illustrate two alternative light sensor unit constructions.
Figure 3B:
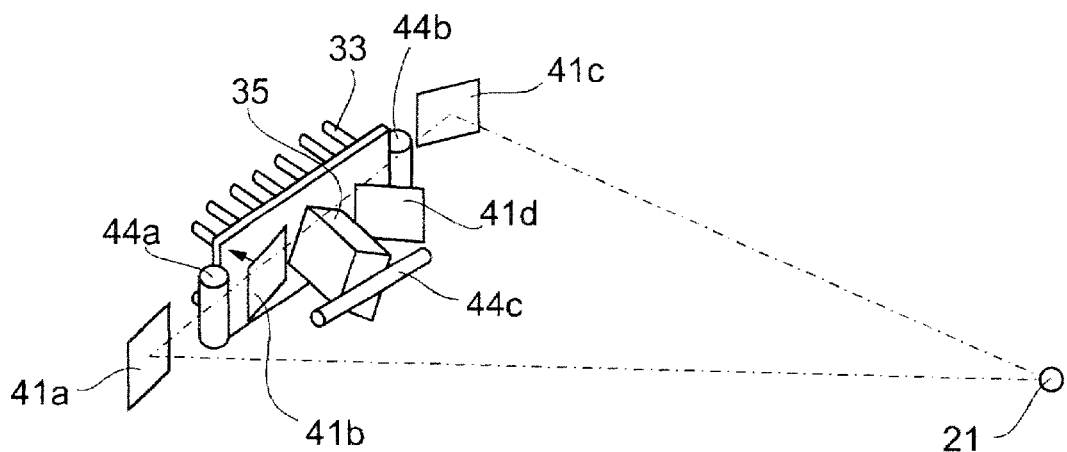
Figure 4A:
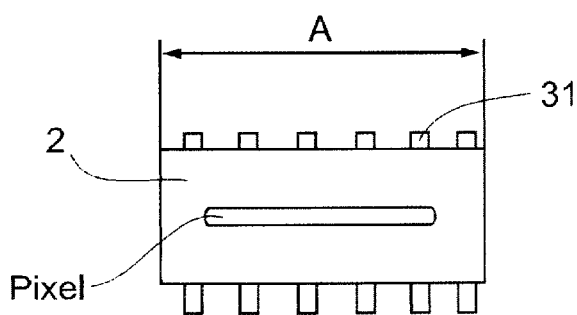
FIG. 4a is a front view.
Figure 4B:
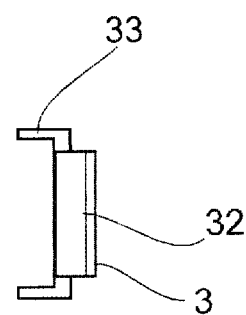
FIG. 4b is a side view, of the light sensor assembly in the light sensor unit of FIGS. 3a and 3b.

The light sensor unit 3 includes a housing, generally designated 30, containing a plurality of components, as more particularly illustrated in FIG. 3. These components include: a light sensor assembly in 31 carrying a plurality of light sensor elements 32 and formed with a plurality of laterally-extending mounting legs 33 for mounting the light sensor unit 3 on the patient's teeth 5; a screen 34 formed with a plurality of slits 34a–34c; and a prism 35 aligned with and interposed between the central group of light sensor elements 32 and the center slit 34c of the screen 34. One example of a light sensor unit that may be employed in the above configuration is Toshiba model TCD 1500C.

Instead of using screen 34 with slits 34a–34c, a cylindrical lens arrangement can be employed, as illustrated in FIG. 3d. In this arrangement, lens 44c performs the function of slit 34c, lens 44b performs the function of slit 34b, and lens 44a performs the function of slit 34a. Moreover, in order to improve detection angles, reflective mirrors 41a and 41b are placed on opposite sides of lens 44a, and reflective mirrors 41c and 41d are placed on opposite sides of lens 44b as will be described hereinafter.

As shown more particularly in FIG. 5a, the light sensor elements 32 define three linear arrays 32a, 32b, and 32c respectively, which extend colinearly along one axis, e.g., the X-axis. The screen 34 is formed with three corresponding linear slits 34a, 34b and 34c. The two end slits 34a, 34b in the screen 34 are aligned with the two end linear arrays 32a, 32b of the light sensor assembly 31 but extend along a second, e.g., the Y-axis. The middle slit 34c of the screen 34 is aligned with the middle array 32c of the light sensor elements 32 and extends parallel to the same longitudinal axis thereof, e.g., the X-axis. As described below, the prism 35, interposed between the middle slit 34c of the screen 34 and the middle array 32c of the light sensor elements 32, is effective to divert light along the Z-axis to the X-axis.

Alternatively, the light can be detected by the sensors utilizing the mirror arrangement illustrated in FIG. 5b. In this configuration, light impinging on mirror 41a is reflected through lens 44a to impinge upon mirror 41b whereupon it is reflected onto the detectors in the area of 32a. Similarly, light impinging on mirror 41c is reflected through lens 44b to impinge upon mirror 41d whereupon it is reflected onto the detectors in the area of 32b.

FIGS. 6–11 illustrate how the foregoing components of the light sensor unit may be used for determining the location in space of each of the three light sources 21, 22, 23 carried by the probe unit 2, and thereby the location in space of the probe contact surface 20 as it is moved from one sample position to another on the outer surface of the tooth 4 being mapped. For this purpose, and as shown in FIG. 2, the X-coordinate will be that of the three linear arrays 32a–32c of the light sensor assembly 32; the Y-coordinate will be that of the two slits 34a, 34b of the screen 34; and the Z-coordinate will be that between the light sensor assembly 31 and the screen 34.

FIGS. 6a, 6b, 6c, 7a and 7b illustrate the manner in which a screen formed with a single slit cooperates with a single linear array of light sensor elements to enable one to determine the angle (α) that a light source, positioned forwardly of the screen, forms with respect to the plane of the screen. For purposes of convenience, only one linear array of light sensor elements 32a is shown, together with the slit 34a in the screen cooperable therewith. These figures show the light sensor unit rotated 90°, such that the light sensor elements 32a extending along the X-axis is disposed vertically; and the slit 34a extending along the Y-axis is disposed horizontally. The spacing between the light sensor elements and the screen along the Z-axis extends horizontally in FIG. 6a.

FIG. 6a illustrates two light sources 21, 22 at different locations along the X-axis. Light source 21 will illuminate light sensor element $i_a$ at one end of array 32a whereas light source 22 will illuminate light sensor element $i_b$ at the other end of array 32a. Since screen slit 34a extends along the Y-axis the location of the light sources in the Y-axis will not affect the light sensor elements in array 32a illuminated by the light sources. As described hereinabove, one can employ cylindrical lenses 44a–44c instead of slits 34a–34c. This alternative arrangement, when used with the mirror arrangement on opposite sides of the lenses allows for an increased amount of light to impinge upon the sensor elements 32a–32c.

Figure 7A:
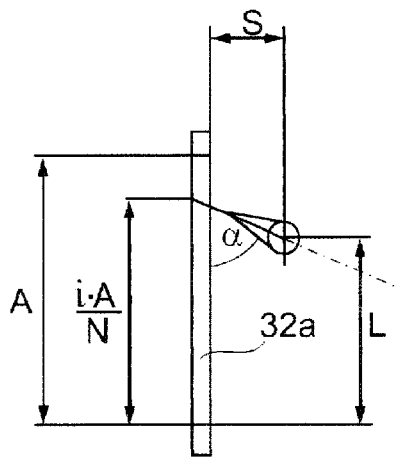
FIGS. 7a, and 8a–8c are optical diagrams.
Figure 7B:
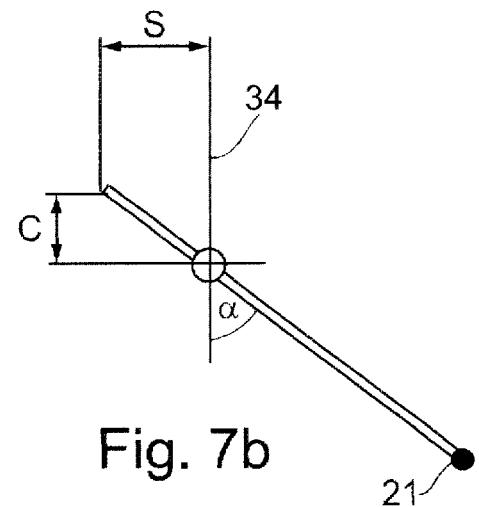

FIGS. 7a and 7b illustrate how the angle α of an illuminating light source 21 may be determined according to the sensor element ($i_a$) illuminated thereby. In FIGS. 7 and 7a, the angle α is the angle formed by the light source with respect to the plane of the screen 34; A is the length of the light sensor array 32a; i is the location of the light sensor element in the array illuminated by the light source 21; N is the number of the light sensor element in the array illuminated by the light source; and S is the distance along the Z-axis between the screen 34 and the light sensor array 32. It will be seen from FIGS. 7 and 7a that:

$$C = \frac{iA}{N} - L \qquad \text{Eq. (1)}$$

and $$\alpha = A\mathrm{Tan}(S/L) \qquad \text{Eq. (2)}$$

Figure 8A:
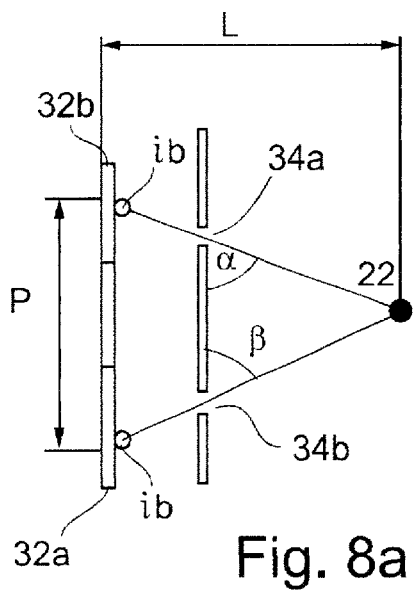

FIGS. 8 and 8a illustrate how two linear arrays of light sensor elements, each cooperable with a slit in the screen, enable a determination to be made of the location in one plane of a light source illuminating a light sensor element in each of the two arrays. Thus one slit (e.g. 34a) cooperable with one sensor element array (e.g. 32a) enables the determination of one angle (e.g. α) as described above with respect to FIGS. 7a and 7b. In a similar manner, the opposite slit (e.g. 34b) cooperable with the opposite sensor array (e.g. 32b) enables the determination of a second angle (e.g., β). By triangulation, these two angles enable the determination of the third angle (χ) and of the exact location in the respective plane (e.g., the XY plane).

Thus, where P is the distance between the illuminated sensor elements in the two arrays 32a, 32b, it can be shown that:

$$\chi = 180° - \alpha - \beta \qquad \text{Eq. (3)}$$

$$L = P \cdot \sin\alpha / \sin\chi \qquad \text{Eq. (4)}$$

because $\dfrac{L}{\sin\alpha} = \dfrac{P}{\sin\chi}$ $$Z = L \cdot \sin\beta \qquad \text{Eq. (5)}$$

$$X = L \cdot \cos\beta \qquad \text{Eq. (6)}$$

Figure 8C:
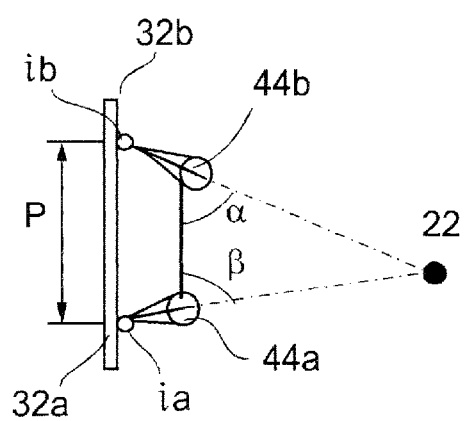
Figure 8B:
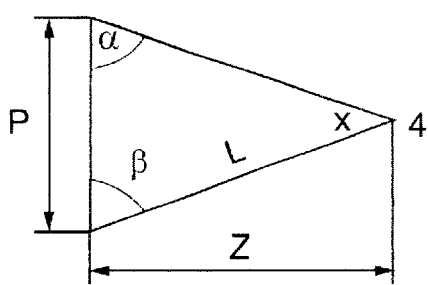

It will be appreciated that the determination of the location of a light source in the manner illustrated in FIGS. 8a and 8b is the location of the light source in one plane, namely in the XY plane in this example. FIG. 8c illustrates the above principle when employing lenses.

FIGS. 9–11a illustrate how the location of a light source in the YZ (or XZ) plane may be made with the light sensor unit 3 illustrated in FIG. 3. This determination is enabled by the provision of the prism 35 aligned with, and in between, the center array 32c of the light sensor elements, and the center slit 34c in the screen 34.

Figure 9A:
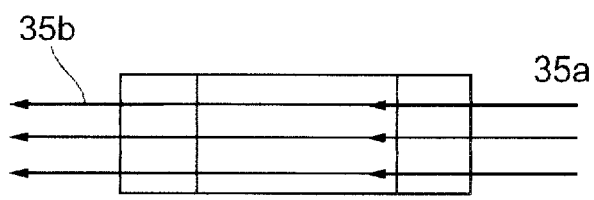
FIGS. 9a–9c illustrates a prism included in the light sensor unit of FIGS. 3a or 3b for determining the location in the third axis of each of the light sources at each of the sampled positions of the probe contact surface.
Figure 9B:
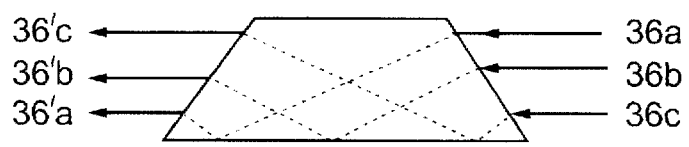
Figure 9C:
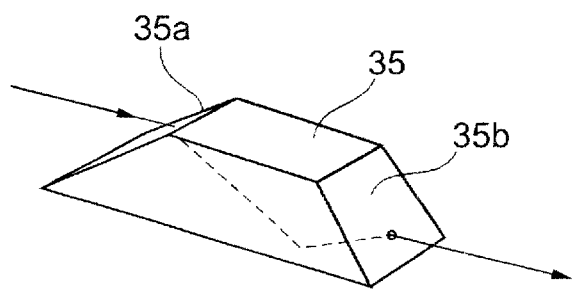

Prism 35, sometimes referred to a Harting-Dove prism, is a direct vision prism made in one piece which inverts the object entering the prism from face 35a to produce an inverted image of the object exiting from the prism $\mathrm{vi}_a$ the opposite face 35b. Thus, as shown in FIGS. 9a and 9b, light rays 36a–36c entering prism 35 via face 35a will be inverted when exiting from the prism via face 35b as shown by the exiting rays 36a'–36c'.

Figure 10A:
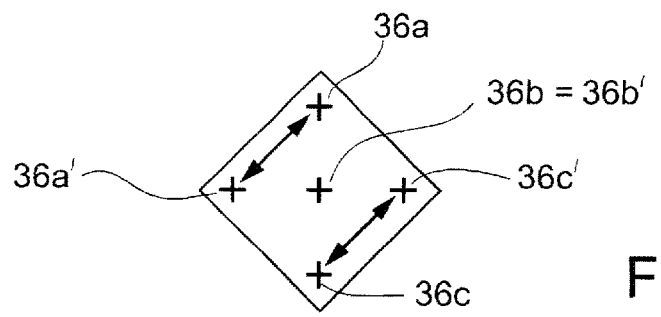
FIGS. 10a–10d are diagrams helpful in explaining the manner in which the prism of FIG. 9, as included in the light sensor unit of FIGS. 3a or 3b, enables the light sensor unit also to determine the location in the third axis of each of the light sources at each of the sample positions of the probe.

As shown in FIG. 10a, if the prism 35 is rotated 45° about the Y-axis, the light rays 36a–36c entering along the Z-axis will be diverted to the X-axis and will be rotated a corresponding amount about the X-axis.

Figure 10B:
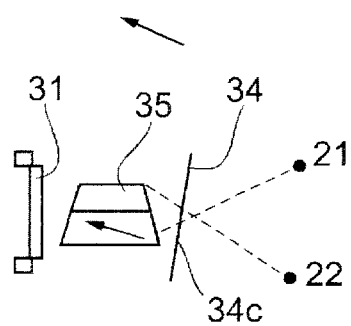
Figure 10C:
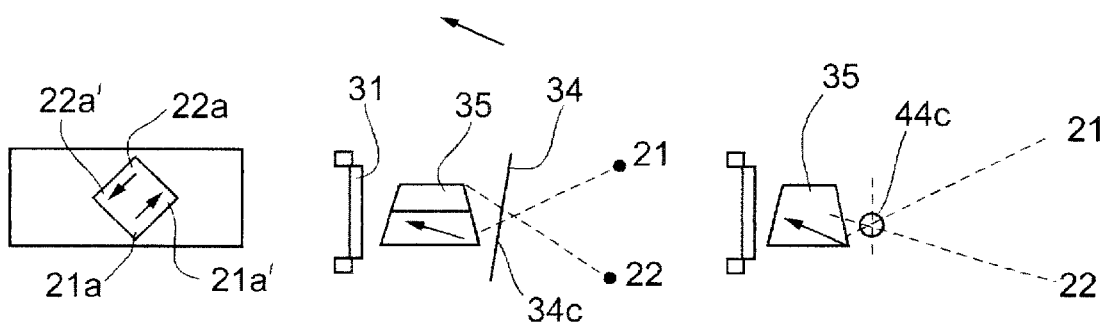
Figure 10D:
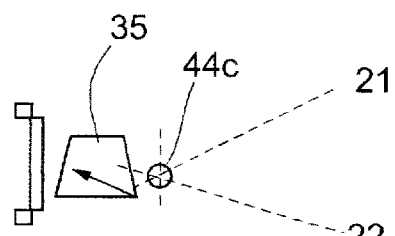

FIGS. 10a and 10b illustrate the light sensor unit 3 of FIG. 3a, except oriented with the sensor elements 32c extending horizontally and the center slit 34c of the screen 34 extending vertically, cooperates with the prism 35 as illustrated in FIGS. 10a–10c, such that the prism 35 diverts incoming rays along the Z-axis to the X-axis. Thus, the light ray from the upper light source 21 will enter the lower part of the prism 35 as shown at 21a in FIG. 10b and will be rotated by the prism 90° to exit at one lateral side of the prism as shown at 21a'; whereas the light ray from the lower light source 22 will enter the prism at the upper side, as shown at 22a, and will be rotated by the prism to exit at the opposite lateral side as shown at 22a'. The location of the light rays along the Z-axis will thus be converted by the prism 35 to a corresponding location along the X-axis. FIG. 10c illustrates the principle when using screen 34 with slits, and FIG. 10d illustrates the principle employing the cylindrical lenses arrangement.

It will thus be seen that the location of each of the three light sources 21, 22, 23, carried by the probe unit 2, can be determined in 3-D space as follows: In the XY plane, its location is the intersection of the lines defined by the angles α and β (FIGS. 8, 8a) determined by the sensor element in each of the two linear arrays 32a, 32b illuminated by the respective light source via the two end slits 34a, 34b of the screen 34; and in the YZ (or XZ) plane, its location is determined by the respective light sensor element illuminated in the center array 32c via the center slit 34c after rotation by the prism 35.

Figure 13:
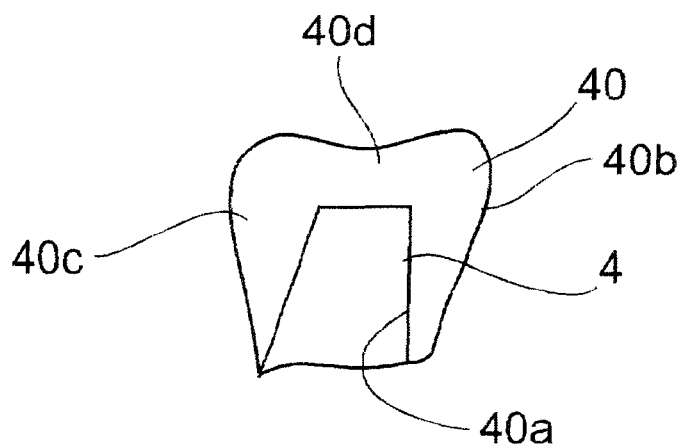
Figure 14:
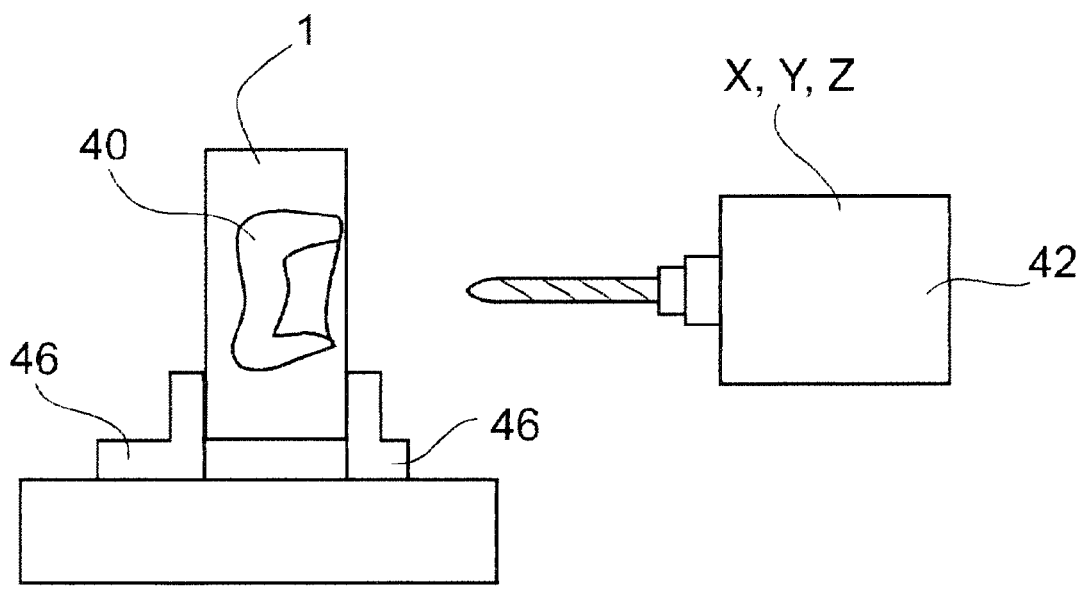

FIGS. 12–14 illustrate the manner in which the above-described apparatus is used for mapping the outer surfaces of teeth for purposes of preparing an artificial dental crown. FIG. 12 illustrates the tooth stump (or implanted post) 4 to receive the crown, the lateral teeth 4a and 4b on the opposite sides of the tooth stump 4, and the opposed teeth 4c overlying the tooth stump. FIG. 13 illustrates the artificial crown, therein designated 40, to be prepared for the tooth stump 4.

For purposes of preparing the crown 40, the above-described apparatus is used for mapping the surface contour of: (a) the tooth stump 4, for preparing the inner surface 40a of the crown; (b) the side surfaces of the teeth 4a and 4c laterally of the tooth stump, for preparing the outer lateral sides 40b, 40c of the crown; and the occlusal surface of the tooth 4c overlying the tooth stump, for preparing the occlusal surface 40d of the crown.

After the foregoing measurements are made, the crown 40 may be prepared by conventional CNC grinder apparatus, generally designated 42 in FIG. 14, which is controlled to grind the workpiece 44, clamped within a mounting member 46, to define the foregoing surfaces 40a, 40b, 40c and 40d of the crown 40.

While the invention has been described with respect to one preferred embodiment, for purposes of preparing a dental crown, it will be appreciated that the invention could be used in other applications for mapping contoured surfaces, and then many other variations, modifications and applications of the invention may be made.

What is claimed is:

1. Apparatus for mapping the contoured surface of a tooth, comprising:
    a probe movable to a plurality of positions over and in contact with the tooth whose surface is to be mapped;
    at least three light sources carried by said probe at different known locations thereof with respect to the contact surface of the probe;
    a light sensor device mountable at a predetermined location in the mouth of a patient whose tooth surface is to be mapped;
    and a computer controlled by said light sensor device for measuring the location in space of each of said light sources at each of said plurality of positions, and for computing from such measurements the location of the probe contact surface at each of said positions.

2. The apparatus according to claim 1, wherein said light sensor device includes a mounting member of a structure for mounting the light sensor device at a predetermined location in a patient's mouth for use in mapping the surface of a tooth to receive an artificial crown.

3. The apparatus according to claim 2, wherein said mounting member is formed with opposed legs for engaging opposed surfaces of the patients teeth spaced from the tooth to receive the crown.

4. The apparatus according to claim 2, wherein said probe further includes a contact detector for detecting the contact of the probe contact surface with the contoured surface to be mapped, and for enabling said computer to measure the locations of said light sources only when said contact detector detects contact of the probe contact surface with said contoured surface.

5. The apparatus according to claim 2, wherein said light sensor device includes:
    first, second and third linear arrays of light sensor elements extending along a first orthogonal axis;
    a screen having first, second and third slits; said first and second slits being aligned with said first and second linear arrays of light sensor elements, respectively, but extending along a second orthogonal axis; said third slit being aligned with said third linear array of light sensor elements and extending along said first orthogonal axis;
    and an optical device between said third linear array of light sensor elements and said third slit for diverting the light received from said light sources in the third orthogonal axis to said first orthogonal axis.

6. The apparatus according to claim 5, wherein said first, second and third linear arrays of light sensor elements are colinear.

7. The apparatus according to claim 5, wherein said optical device is a prism.

8. A method of mapping a contoured surface, comprising:
    providing a probe for contacting the contoured surface with at least one light source at a known location with respect to the probe contact surface;
    providing a light sensor device at a known location with respect to said contoured surface to be mapped;
    moving said probe over said contoured surface through a plurality of positions with the probe contact surface in contact with the contoured surface at each of said positions;
    measuring the location in space of each light source at each of said positions;
    and computing, from the measured location of said light source at each of said positions, the location of the probe contact surface with respect to said known location of thee light sensor device.

9. The method according to claim 8, wherein said probe is provided with at least three light sources at different known locations with respect to said probe contact surface.

10. The method according to claim 8, wherein said light sensor device includes:
    first, second and third linear arrays of light sensor elements extending along a first axis;
    a screen having first, second and third slits; said first and second silts being aligned with said first and second linear arrays of light sensor elements, respectively, but extending along a second axis; said third, slit being aligned with said third linear array of light sensor elements and extending along said first axis;
    and an optical device between said third linear array of light sensor elements and said third slit for diverting the light received from said light sources in the third axis to said first axis.

11. The method according to claim 10, wherein said first, second and third linear arrays of light sensor elements are colinear.

12. The method according to claim 10, wherein said optical device is a prism.

13. The method according to claim 10, wherein said light sensor device is mounted in the mouth of person for use in mapping the surfaces of teeth for purposes of preparing an artificial crown.

14. The method according to claim 12, wherein said light sensor device is mounted on teeth spaced from a tooth stump to receive the artificial crown, and said probe is used for mapping the, surface contour of:
    (a) the tooth stump, for preparing the inner surface of the crown;
    (b) the teeth laterally of the tooth stump, for preparing the outer lateral sides of the crown; and
    (c) the occlusal surface of the tooth overlying the tooth stump, for preparing the outer occlusal surface of the crown.

15. Apparatus for mapping a contoured surface, comprising:
    a probe movable to a plurality of positions, over and in contact with the contoured surface to be mapped;
    at least one light source carried by said probe at a location thereof with respect to the contact surface of the probe;
    a light sensor device mountable at a predetermined location with respect to said contoured surface to be mapped;
    and a computer controlled by said light sensor device for measuring the location in space of each light source at each of said plurality of positions, and for computing from such measurements the location of the probe contact surface at each of said positions.

16. The apparatus according to claim 15, wherein said probe further includes a contact detector for detecting the contact of the probe contact surface with the contoured surface to be mapped, and for enabling said computer to measure the locations of said light source only when said contact detector detects contact of the probe contact surface with said contoured surface.

17. The apparatus according to claim 15, wherein said probe includes at least three light sources at different known locations with respect to said probe contact surface.

18. The apparatus according to claim 15, wherein said light sensor device includes:

first, second and third linear arrays of light sensor elements extending along a first orthogonal axis;

a screen having first, second and third slits; said first and second slits being aligned with said first and second linear arrays of light sensor elements, respectively, but extending along a second orthogonal axis; said third slit being aligned with said third linear array of light sensor elements and extending along said first orthogonal, axis;

and an optical device between said third linear array of light sensor elements and said third slit for diverting the light received from said light sources in the third orthogonal axis to said first orthogonal axis.

19. The apparatus according to claim 18, wherein said first, second and third linear arrays of light sensor elements are colinear.

20. The apparatus according to claim 18, wherein said third slit is between said first and second slits, and said third array of light sensor elements is between said first and second arrays of light sensor elements.

21. The apparatus according to claim 18, wherein said optical device is a prism.

22. The apparatus according to claim 15, wherein said light sensor device includes a mounting member of a structure for mounting the light sensor device at a predetermined location in a patient's mouth for use in mapping the surface of a tooth to receive an artificial crown.

23. The apparatus according to claim 22, wherein said mounting member is formed with opposed legs for engaging opposed surfaces of the patients teeth spaced from the tooth to receive the crown.

* * * * *